US008772465B2

(12) United States Patent
Matsui et al.

(10) Patent No.: US 8,772,465 B2
(45) Date of Patent: Jul. 8, 2014

(54) IRES FUNCTIONING IN PLANT

(75) Inventors: Minami Matsui, Kanagawa (JP);
Yoshiharu Yamamoto, Kanagawa (JP);
Kazuhito Gohda, Kanagawa (JP);
Kumiko Suzuki, Kanagawa (JP)

(73) Assignee: Riken, Saitama (JP)

( * ) Notice: Subject to any disclaimer, the term of this patent is extended or adjusted under 35 U.S.C. 154(b) by 1444 days.

(21) Appl. No.: 10/586,052

(22) PCT Filed: Jan. 13, 2005

(86) PCT No.: PCT/JP2005/000283
§ 371 (c)(1),
(2), (4) Date: Jul. 14, 2006

(87) PCT Pub. No.: WO2005/068631
PCT Pub. Date: Jul. 28, 2005

(65) Prior Publication Data
US 2008/0057581 A1    Mar. 6, 2008

(30) Foreign Application Priority Data

Jan. 15, 2004 (JP) ................. 2004-008025

(51) Int. Cl.
*C12N 15/82* (2006.01)
*C07H 21/04* (2006.01)
*A01H 5/00* (2006.01)

(52) U.S. Cl.
USPC ...... 536/24.1; 536/23.1; 435/320.1; 800/278; 800/295; 800/298

(58) Field of Classification Search
None
See application file for complete search history.

(56) References Cited

U.S. PATENT DOCUMENTS

| | | | |
|---|---|---|---|
| 5,906,961 A | 5/1999 | Roberts et al. | |
| 2003/0051261 A1 | 3/2003 | Vanderhaeghen et al. | |
| 2003/0084482 A1 | 5/2003 | Hall et al. | |
| 2003/0084484 A1 | 5/2003 | Bascomb et al. | |
| 2004/0014216 A1 | 1/2004 | Gleba et al. | |
| 2004/0031072 A1* | 2/2004 | La Rosa et al. | 800/278 |
| 2004/0055037 A1 | 3/2004 | Gleba et al. | |

FOREIGN PATENT DOCUMENTS

| | | |
|---|---|---|
| EP | 1033405 | 9/2000 |
| JP | 2003-070477 | 3/2003 |
| WO | 0159138 | 8/2001 |
| WO | 02/068664 | 9/2002 |
| WO | 02/083867 | 10/2002 |
| WO | 02/029068 | 11/2002 |
| WO | 02/101006 | 12/2002 |
| WO | 03/012035 A2 | 2/2003 |

OTHER PUBLICATIONS

Alonso et al. A sequence-indexed library of insertion mutations in the arabidopsis genome. (2002) GenBank Accession BH789726, pp. 1-2.*
Urwin et al. Functional characterization of the EMCV IRES in plants. (2000) The Plant Journal; vol. 24, pp. 583-589.*
Akbergenov et al. ARC-1, a sequence element complementary to an internal 18S rRNA segment, enhances translation efficiency in plants when present in the leader or intercistronic region of mRNAs. (2004) Nucleic Acids Research; vol. 32, pp. 239-247.*
Hamby et al. Cabomba caroliniana 18S ribosomal RNA (18S rRNA), ca. bp 981 to 1124 in mature rRNA. (2002) GenBank Accession No. M82734.1; pp. 1-2.*
P. Hajdukiewicz et al., " The Small, Versatile pPZP Family of Agrobacterium Binary Vectors for Plant Transformation", Plant Molecular Biology, vol. 25, pp. 989-994 (1994).
R. Jefferson et al., "GUS Fusions: ÿ-Glucuronidase as a Sensitive and Versatile Gene Fusion Marker in Higher Plants", EMBO J., vol. 6, No. 13, pp. 3901-3907 (1987).
D. Frisch et al., "Complete Sequence of the Binary Vector Bin 19," Plant Molecular Biology, vol. 27, pp. 405-409 (1995).
S. Clough et al., "Floral Dip: A Simplified Method for Agrobacterium-mediated Transformation of *Arabidopsis thaliana*", Plant J., vol. 16, No. 6, pp. 735-743 (1998).
R.Z. Akbergenov et al., ARC-1, a sequence element complementary to an internal 18S rRNA segment, enhances translation efficiency in plants when present in the leader or intercistronic region of mRNAs, Nucleic Acids Res., vol. 32, No. 1, Jan. 12, 2004, pp. 239-247.
Y.Y. Yamamoto et al., Gene trapping of the *Arabidopsis* genome with a firefly luciferase reporter, Plant J., vol. 35, 2003, pp. 273-283.
P.A. Ivanov et al., A Tobamovirus genome that contains an internal ribosome entry site functional in vitro, Virology, vol. 232, 1997, pp. 32-43.
P. Urwin et al., Functional characterization of the EMCV IRES in plants, Plant J., vol. 24, No. 5, 2000, pp. 583-589.
W. Zhou et al., Transcript leader regions of two *Saccharomyces cerevisiae* mRNAs contain internal ribosome entry sites that function in living cells, Proc. Natl. Acad. Sci., vol. 98, No. 4, 2001, pp. 1531-1536.
W. Zhou et al., Isolation and identification of short nucleotide sequences that effect translation initiation in *Saccharomyces cerevisiae*, Proc. Natl. Acad. Sci., vol. 100, No. 8, 2003, pp. 4457-4462.
A.H. Jheon et al., Characterization of the 5'-flanking region of rat AJ18 gene, Gene, vol. 310, 2003, pp. 203-213.
S.A. Chappell et al., A 9-nt segment of a cellular mRNA can function as an internal ribosome entry sties (IRES) and when present in linked multiple copies greatly enhances IRES activity, Proc. Natl. Acad. Sci., vol. 97, No. 4, 2000, pp. 1536-1541.

(Continued)

*Primary Examiner* — Cathy Kingdon Worley
(74) *Attorney, Agent, or Firm* — Greenblum & Bernstein, P.L.C.

(57) ABSTRACT

It is intended to provide for a polycistronic expression pattern in a plant used as a host. The present invention provides a polynucleotide which comprises the following DNA (a) or (b) and functions as an IRES (internal ribosome entry site) in a plant: (a) DNA of the nucleotide sequence represented by SEQ ID NO: 1, 2, 3, or 4; or (b) DNA of a nucleotide sequence derived from the nucleotide sequence represented by SEQ ID NO: 1, 2, 3, or 4 by the substitution, deletion, addition, and insertion of one or more bases and having a function of positively regulating the translation of a nucleic acid located downstream thereof.

8 Claims, 4 Drawing Sheets

(56) References Cited

OTHER PUBLICATIONS

M. Kimura et al., *Arabidopsis* transcriptional regulation by light stress via hydrogen peroxide-dependent and -independent pathways, Genes Cells, vol. 6, 2001, pp. 607-617.

English language Abstract of JP 2003-070477.

Abbott et al., "The Sequence of Homo Sapiens BAC clone RP11-791G15," EMBL Sequence Database, EBI (Online), Accession No. AC092687, Jul. 25, 2001.

Borman et al., "Comparison of Picornaviral IRES-Driven Internal Initiation of Translation in Cultured Cells of Different Origins" *Nucleic Acids Research*, vol. 25, No. 5, p. 925-932, 1997.

Matsuo et al., "Characterization of the EMCV-IRES Mediated Bicistronic Translation in Plant Cells" *Plant Biotechnology*, vol. 21, No. 2, p. 119-126, 2004.

* cited by examiner

Fig. 1

| | | | | | | |
|---|---|---|---|---|---|---|
| arabidopsis 18s rRNA | GATCAGCGGGA | TGTTGC-TTA | TAGGACTCCG | CTGGC-ACCT | T-ATGAGAAA | TCAAAGTTTT |
| soybean 18s rRNA | GATCAGCGGGA | TGTTGC-TTT | TAGGACTCCG | CTGGC-ACCT | T-ATGAGAAA | TCAAAGTCTT |
| petunia 18s rRNA | GATCAGCGGGA | TGTTGC-TTT | TAGGACTCCG | CTGGC-ACCT | T-ATGAGAAA | TCAAAGTTTT |
| tomato 17s rRNA | GATCGGCGGGA | TGTTGC-TTT | TAGGACTCCG | CCGGC-ACCT | T-ATGAGAAA | TCAAAGTTTT |
| Antirrhinum 18s rRNA | GATCGGCGGGA | TGTTGC-TTT | TAGGACTCCG | CCGGC-ACCT | T-ATGAGAAA | TCAAAGTCTT |
| tobacco 18s rRNA | GATCGGCGGGA | TGTTGC-TTT | TAGGACTCCG | CCGGC-ACCT | T-ATGAGAAA | TCAAAGTTTT |
| rice 18s rRNA | GATCGGCGGGA | TGTTGC-TTA | TAGGACTCCG | CCGGC-ACCT | T-ATGAGAAA | TCAAAGTCTT |
| maize 17s rRNA | GATCAGCGG- | TGTTAC-TAA | TAGGACCCCG | CTGGCCACCT | T-ATGAGAAA | TCAAAGTTTT |
| M.polymorpha 18S rRNA | GATCGGCGGGA | TGTTAA-TTT | GATGACTCCG | CCGGC-ACCT | CCATGAGAAA | TCAAAGTTTT |
| P.patens 18S rRNA | GATCGGCGGGA | TGTTAC-TTT | GATGACTCCG | CCAGC-ACCT | T-ATGAGAAA | TCAAAGTTTT |
| Chlamydomonas 18s rRNA | GATTGGCAGG | TGTTCC-TTT | GATGACCCTG | CCAGC-ACCT | T-GAGAGAAA | TCAGAGTCTT |
| Synechocystis 16s rRNA | ------G | CGTGGCTTGT | ATCGACCCGA | GCCGT-GCC- | ------GAAG | CTAACGCGTT |
| Saccharomyces cerevisiae 18s rRNA | -ATCGGGTGG | TGTTTT-TTT | AATGACCCAC | TCGGT-ACCT | T-ACGAGAAA | TCAAAGTCTT |
| Schizosaccharomyces pombe18s rRNA | GATCGGGCAA | TGTTTCATTT | ATCGACTTGC | TCGGC-ACCT | T-ACGAGAAA | TCAAAGTCTT |
| mouse 18s rRNA | GATGCGGCGG | CGTTAT-TCC | CATGACCCGC | CGGGCAGCTT | C--CGGGAAA | CCAAAGTCTT |
| rat 18s rRNA | GATGCGGCGG | CGTTAT-TCC | CATGACCCGC | CGGGCAGCTT | C--CGGGAAA | CCAAAGTCTT |
| human 18s rRNA | GATGCGGCGG | CGTTAT-TCC | CATGACCCGC | CGGGCAGCTT | C--CGGGAAA | CCAAAGTCTT |

The R bracket spans the columns: TAGGACTCCG and CTGGC-ACCT (and corresponding rows).

IRES FUNCTIONING IN PLANT

TECHNICAL FIELD

The present invention relates to a polynucleotide which functions as IRES (internal ribosome entry site) in a plant and to an expression unit thereof. The present invention also relates to an expression vector comprising the expression unit and to a method of regulating gene expression in a plant by use of the expression unit. Background Art While eukaryotic cells such as animal cells generally have a monocistronic expression pattern, some genes are known to be expressed following a polycistronic pattern. The polycistronic expression pattern involves plural regions encoding proteins and regions for ribosomal protein rebinding (IRES: internal ribosome entry site) located between adjacent coding regions.

IRES found in animal cells permits for polycistronic expression in eukaryotes and as such, is used in a variety of expression vectors for animal cells. For example, a certain expression vector for animal cells, which comprises a marker gene inserted downstream of IRES, can be examined for the expression of a gene located upstream of the IRES by observing the expression of the marker gene. This expression vector for animal cells does not require fusing a protein target of expression analysis and a marker protein.

However, when plant cells or plant bodies are used as hosts, a vector having an IRES-like function as described above has not been developed so far. In other words, expression vectors that achieve polycistronic expression in plant cells and plant bodies used as hosts are unknown.

Non-Patent Document 1: Chappell S A, Edelman G M, Mauro V P, A 9-nt segment of a cellular mRNA can function as an internal ribosome entry site (IRES) and when present in linked multiple copies greatly enhances IRES activity. PNAS 97, 1536-1541.

Non-Patent Document 2: Urwin P, Yi L, Martin H, Atkinson H, Gilmartin P M, Functional characterization of the EMCV IRES in plants. Plant J. 24, 583-589

DISCLOSURE OF THE INVENTION

Thus, in light of these situations, an object of the present invention is to provide DNA, an expression unit, and an expression vector, which permit for a polycistronic expression pattern in a plant used as a host.

To attain the object, the present inventor has conducted diligent studies and has consequently completed the present invention by successfully finding a novel IRES that functions in a plant.

More specifically, the present invention encompasses the following inventions:

(1) a polynucleotide which functions as IRES (internal ribosome entry site) in a plant and comprises the following DNA (a) or (b):
(a) a DNA of the nucleotide sequence represented by SEQ ID NO: 1, 2, 3, or 4; or
(b) a DNA of a nucleotide sequence derived from the nucleotide sequence represented by SEQ ID NO: 1, 2, 3, or 4 by the substitution, deletion, addition, and insertion of one or more bases and having a function of positively regulating the translation of a gene located downstream along the translation direction in the plant.
(2) The polynucleotide according to (1), wherein repeats of the DNA (a) or (b) are linked via or without a spacer sequence.
(3) The polynucleotide according to (2), wherein the number of the repeats of the DNA (a) or (b) is 7 to 10.
(4) The polynucleotide according to any one of (1) to (3), wherein the polynucleotide further comprises at least a gene and/or a promoter.
(5) The vector comprising a polynucleotide according to any one of (1) to (4).
(6) A transformant transformed with a polynucleotide according to any one of (1) to (4) or with a vector according to (5).
(7) A transgenic plant having a polynucleotide according to any one of (1) to (4) incorporated in the genome.
(8) A method of regulating gene expression in a plant, comprising the steps of: constructing a polynucleotide according to any one of (1) to (4) or a vector according to (5); and transforming the polynucleotide or the vector into a plant-derived host, wherein the translation of a gene located downstream of the DNA (a) or (b) is positively regulated in the transformed plant-derived host.

EFFECTS OF THE PRESENT INVENTION

According to the present invention, a polynucleotide which functions as IRES in a plant and comprises novel DNA can be provided. Polycistronic expression can be achieved in a plant by using the polynucleotide according to the present invention.

The present specification encompasses the contents described in the specification and/or drawings of Japanese Patent Application No. 2004-008025 that serves as the basis of the priority of the present application.

BRIEF DESCRIPTION OF THE DRAWINGS

FIG. 1 is a diagram comparing a nucleotide sequence containing the given region of 18S rDNA among a variety of organisms (SEQ ID NOS 21-37, respectively, in order or appearance);

BEST MODE FOR CARRYING OUT THE INVENTION

Figure 2:
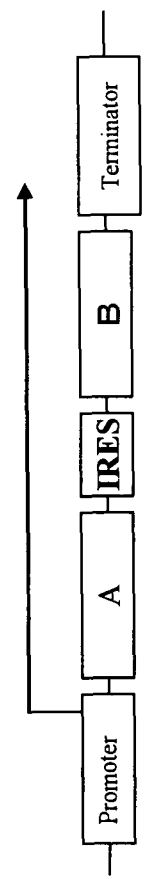
FIG. 2 is a diagram showing the constitution of an expression vector to which the present invention is applied.

Hereinafter, the present invention will be described in detail with reference to drawings.

1-1. Polynucleotide According to the Present Invention

A polynucleotide according to the present invention comprises the following DNA (a) and/or (b) and has a function of positively controlling the translation of a gene located downstream of the DNA in a plant:
(a) DNA consisting of the nucleotide sequence represented by SEQ ID NO: 1; and
(b) DNA consisting of a nucleotide sequence derived from the nucleotide sequence represented by SEQ ID NO: 1 by the substitution, deletion, addition, and insertion of one or more bases and having a function of positively regulating the translation of a gene located downstream along the translation direction.

In other words, the polynucleotide according to the present invention can permit the binding thereto of ribosome that plays a central role in the translation mechanism of a host, and has a function of achieving the translation of a gene located downstream through the translation mechanism of the host. A DNA region having such a function is generally called IRES (internal ribosome entry site). Hereinafter, the polynucleotide according to the present invention is therefore referred to as IRES.

In this context, the nucleotide sequence represented by SEQ ID NO: 1 is a sequence designed to be complementary in the reverse direction to the given region of Arabidopsis 18S rDNA. Moreover, the term "downstream" means lying more posterior with respect to the transcription direction (i.e., a direction from the 5' terminus toward the 3' terminus in a DNA strand to be transcribed). The phrase "positively controlling the translation" means, in other words, improving translation efficiency and means that ribosome binding promotes the translation of a coding region located downstream. In the description below, the function of positively controlling the translation is simply called "control ability".

In the DNA (b), the several bases mean preferably 2 to 5 bases, more preferably 2 to 3 bases, in the nucleotide sequence represented by SEQ ID NO: 1. In the nucleotide sequence represented by SEQ ID NO: 1, it is particularly preferred that a position capable of the substitution, deletion, addition, and insertion should be selected from bases at the 4th to 10th positions and a base at the 12th position. In SEQ ID NO: 1, G at the 1st position may be substituted by A; C at the 3rd position may be substituted by T or G; A at the 4th position may be substituted by G or C; G at the 5th position may be substituted by C or A; C at the 6th position may be substituted by G or T; G at the 7th position may be substituted by A, C, or T; G at the 8th position may be substituted by A; and A at the 9th position may be substituted by G.

Examples of the nucleotide sequence derived from the nucleotide sequence represented by SEQ ID NO: 1 by the substitution of one or more bases can include the following nucleotide sequences (SEQ ID NOS: 5 to 20):

```
SEQ ID NO: 5:      GCCAGCGGAGTC
SEQ ID NO: 6:      GCCAGCGGAGTC
SEQ ID NO: 7:      GCCGGCGGAGTC
SEQ ID NO: 8:      GCCGGCGGAGTC
SEQ ID NO: 9:      GCCGGCGGAGTC
SEQ ID NO: 10:     GCCGGCGGAGTC
SEQ ID NO: 11:     GCCAGCGGGGTC
SEQ ID NO: 12:     GCCGGCGGAGTC
SEQ ID NO: 13:     GCTGGCGGAGTC
SEQ ID NO: 14:     GCTGGCAGGGTC
SEQ ID NO: 15:     ACGGCTCGGGTC
SEQ ID NO: 16:     ACCGAGTGGGTC
SEQ ID NO: 17:     GCCGAGCAAGTC
SEQ ID NO: 18:     GCCCGGCGGGTC
SEQ ID NO: 19:     GCCCGGCGGGTC
SEQ ID NO: 20:     GCCCGGCGGGTC
```

Thus, these nucleotide sequences represented by SEQ ID NOS: 5 to 20 are encompassed by the DNA (b). The nucleotide sequence of SEQ ID NO: 5 is a sequence designed as a chain complementary in the reverse direction to the given region of soybean 18S rDNA. The nucleotide sequence of SEQ ID NO: 6 is a sequence designed as a chain complementary in the reverse direction to the given region of petunia 18S rDNA. The nucleotide sequence of SEQ ID NO: 7 is a sequence designed as a chain complementary in the reverse direction to the given region of tomato 18S rDNA. The nucleotide sequence of SEQ ID NO: 8 is a sequence designed as a chain complementary in the reverse direction to the given region of antirrhinum 18S rDNA. The nucleotide sequence of SEQ ID NO: 9 is a sequence designed as a chain complementary in the reverse direction to the given region of tobacco 18S rDNA. The nucleotide sequence of SEQ ID NO: 10 is a sequence designed as a chain complementary in the reverse direction to the given region of rice 18S rDNA. The nucleotide sequence of SEQ ID NO: 11 is a sequence designed as a chain complementary in the reverse direction to the given region of maize 18S rDNA. The nucleotide sequence of SEQ ID NO: 12 is a sequence designed as a chain complementary in the reverse direction to the given region of *M. polymorpha* 18S rDNA. The nucleotide sequence of SEQ ID NO: 13 is a sequence designed as a chain complementary in the reverse direction to the given region of *Physcomitrella patens* 18S rDNA. The nucleotide sequence of SEQ ID NO: 14 is a sequence designed as a chain complementary in the reverse direction to the given region of *Chlamydomonas* 18S rDNA. The nucleotide sequence of SEQ ID NO: 15 is a sequence designed as a chain complementary in the reverse direction to the given region of *Synechocystis* 18S rDNA. The nucleotide sequence of SEQ ID NO: 16 is a sequence designed as a chain complementary in the reverse direction to the given region of *Saccharomyces cerevisiae* 18S rDNA. The nucleotide sequence of SEQ ID NO: 17 is a sequence designed as a chain complementary in the reverse direction to the given region of *Schizosaccharomyces pombe* 18S rDNA. The nucleotide sequence of SEQ ID NO: 18 is a sequence designed as a chain complementary in the reverse direction to the given region of mouse 18S rDNA. The nucleotide sequence of SEQ ID NO: 19 is a sequence designed as a chain complementary in the reverse direction to the given region of rat 18S rDNA. The nucleotide sequence of SEQ ID NO: 20 is a sequence designed as a chain complementary in the reverse direction to the given region of human 18S rDNA. These nucleotide sequences containing the given sequence of 18S rDNA in a variety of organisms are shown in FIG. 1. In FIG. 1, the given regions serving as sources for designing the nucleotide sequences of SEQ ID NOS: 1 and 5 to 20 are indicated by R.

On the other hand, the DNA (b) encompasses DNA consisting of a nucleotide sequence hybridizing under stringent conditions to a nucleotide sequence complementary to the nucleotide sequence represented by SEQ ID NO: 1. The stringent conditions refer to conditions under which so-called specific hybrids are formed. To be more specific, the stringent conditions refer to conditions at a sodium concentration of 15 to 300 mM, preferably 15 to 75 mM and a temperature of 50 to 60° C., preferably 55 to 60° C.

On the other hand, whether or not DNA having a given nucleotide sequence possesses the control ability can be determined by constructing a vector having the DNA target with a reporter gene incorporated downstream thereof, and then transforming a plant with the vector to compare the expression level of the reporter gene in the obtained transgenic plant with that in a control. Any reporter gene may be used. For example, a GUS gene encoding β-glucuronidase, a Luc gene encoding luciferase, or a GFP gene encoding a green fluorescent protein can be used.

The IRES can be obtained by chemical synthesis on the basis of SEQ ID NO: 1. In the nucleotide sequence represented by SEQ ID NO: 1, the substitution, deletion, addition, and insertion of one or more bases can be carried out by an approach known in the art such as the Kunkel method or the gapped duplex DNA method, or a similar method. For example, a mutagenesis kit utilizing site-specific mutagenesis (e.g., Mutant-K (manufactured by TAKARA) and Mutant-G (manufactured by TAKARA)) or LA PCR in vitro Mutagenesis series kit (manufactured by TAKARA) is used for mutagenesis.

1-2. Polynucleotide According to the Present Invention

A polynucleotide according to the present invention comprises the following DNA (a) and/or (b) and has a function of positively controlling the translation of a gene located downstream of the DNA in a plant:
(a) DNA consisting of the nucleotide sequence represented by SEQ ID NO: 2 or 3; and
(b) DNA consisting of a nucleotide sequence derived from the nucleotide sequence represented by SEQ ID NO: 2 or 3 by the substitution, deletion, addition, and insertion of one or more bases and having a function of positively regulating the translation of a gene located downstream along the translation direction in a plant.

In the DNA (b), the several bases mean preferably 1 to 20 bases, more preferably 1 to 5 bases, in the nucleotide sequence represented by SEQ ID NO: 2 or 3. The DNA (b) encompasses DNA consisting of a nucleotide sequence hybridizing under stringent conditions to a nucleotide sequence complementary to the nucleotide sequence represented by SEQ ID NO: 2 or 3. The stringent conditions refer to conditions under which so-called specific hybrids are formed. To be more specific, the stringent conditions refer to conditions at a sodium concentration of 15 to 300 mM, preferably 15 to 75 mM and a temperature of 50 to 60° C., preferably 55 to 60° C.

On the other hand, whether or not a polynucleotide having a given nucleotide sequence possesses the control ability can be determined by constructing a vector having the polynucleotide target with a reporter gene incorporated downstream thereof, and then transforming a plant with the vector to compare the expression level of the reporter gene in the obtained transgenic plant with that in a control. Any reporter gene may be used. For example, a GUS gene encoding β-glucuronidase, a Luc gene encoding luciferase, or a GFP gene encoding a green fluorescent protein can be used.

The IRES can be obtained by chemical synthesis on the basis of SEQ ID NO: 2 or 3. Alternatively, the IRES can also be obtained by PCR using the MP region of tobamovirus genome as a template. In the nucleotide sequence represented by SEQ ID NO: 2 or 3, the substitution, deletion, addition, and insertion of one or more bases can be carried out by an approach known in the art such as the Kunkel method or the gapped duplex DNA method, or a similar method. For example, a mutagenesis kit utilizing site-specific mutagenesis (e.g., Mutant-K (manufactured by TAKARA) and Mutant-G (manufactured by TAKARA)) or LA PCR in vitro Mutagenesis series kit (manufactured by TAKARA) is used to introduce mutation.

1-3. Polynucleotide According to the Present Invention

A polynucleotide according to the present invention comprises the following DNA (a) and/or (b) and has a function of positively controlling the translation of a gene located downstream of the DNA in a plant:
(a) DNA consisting of the nucleotide sequence represented by SEQ ID NO: 4; and
(b) DNA consisting of a nucleotide sequence derived from the nucleotide sequence represented by SEQ ID NO: 4 by the substitution, deletion, addition, and insertion of one or more bases and having a function of positively regulating the translation of a gene located downstream along the translation direction in a plant.

In the DNA (b), the several bases mean preferably 1 to 20 bases, more preferably 1 to 5 bases, in the nucleotide sequence represented by SEQ ID NO: 4. The DNA (b) encompasses DNA consisting of a nucleotide sequence hybridizing under stringent conditions to a nucleotide sequence complementary to the nucleotide sequence represented by SEQ ID NO: 4. The stringent conditions refer to conditions under which so-called specific hybrids are formed. To be more specific, the stringent conditions refer to conditions at a sodium concentration of 15 to 300 mM, preferably 15 to 75 mM and a temperature of 50 to 60° C., preferably 55 to 60° C.

On the other hand, whether or not a polynucleotide having a given nucleotide sequence possesses the control ability can be determined by constructing a vector having the polynucleotide target with a reporter gene incorporated downstream thereof, and then transforming a plant with the vector to compare the expression level of the reporter gene in the obtained transgenic plant with that in a control. Any reporter gene may be used. For example, a GUS gene encoding β-glucuronidase, a Luc gene encoding luciferase, or a GFP gene encoding a green fluorescent protein can be used.

The IRES can be obtained by chemical synthesis on the basis of SEQ ID NO: 4. Alternatively, the IRES can also be obtained by PCR using the CP region of tobamovirus genome as a template. In the nucleotide sequence represented by SEQ ID NO: 4, the substitution, deletion, addition, and insertion of one or more bases can be carried out by an approach known in the art such as the Kunkel method or the gapped duplex DNA method, or a similar method. For example, a mutagenesis kit utilizing site-specific mutagenesis (e.g., Mutant-K (manufactured by TAKARA) and Mutant-G (manufactured by TAKARA)) or LA PCR in vitro Mutagenesis series kit (manufactured by TAKARA) is used for mutagenesis.

2. Expression Unit

The polynucleotide according to the present invention can be functional by taking the form of an expression unit having the IRES described in the paragraphs "1-1 to -3. Polynucleotide according to the present invention". The expression unit can comprise the IRES described in the paragraphs "1-1 to -3. Polynucleotide according to the present invention" and at least a promoter and/or a gene.

The expression unit means and encompasses those incorporated in the chromosome of a host, those incorporated into a vector or the like, or a DNA fragment. This expression unit can reliably translate a gene located downstream of the IRES in a host and can construct an unprecedented polycistronic gene expression system in a plant.

For example, the expression unit may be a DNA fragment comprising the IRES and the gene arranged in this order. The expression unit may be the DNA fragment comprising the IRES and the gene arranged in this order, which is inserted in, for example the T region of a Ti plasmid or is not inserted into a vector such as a plasmid. In this case, the expression unit may comprise the promoter upstream of the IRES. The expression unit thus constituted can be incorporated into the genome of a host and thereby positively control the translation of the gene located downstream of the IRES.

Alternatively, the expression unit may be a DNA fragment comprising the gene and the IRES arranged in this order. This expression unit may also be the DNA fragment, which is incorporated or not inserted in a vector such as a plasmid. In this case, an existing gene in the genome of a host is located downstream of the IRES as a result of incorporation of the expression unit into the genome of the host. In this state, the IRES can positively control the translation of the gene located downstream thereof. The expression unit, which comprises the gene (e.g., a reporter gene) arranged downstream or upstream of the IRES, is specifically used in the observation of, for example the expression status of any gene (hereinafter, the "gene of interest") retained in the host. To be more specific, the synchronized expression of the gene of interest and the reporter gene can be achieved by incorporating this expression unit by use of an approach such as homologous recombination so that the expression unit is expressed by a promoter of the gene of interest. This produces the effect of allowing for the understanding of the temporal and spatial expression pattern of the gene of interest.

Alternatively, the expression unit may be a DNA fragment comprising the promoter, the gene (e.g., a reporter gene), and the IRES arranged in this order. When this expression unit is incorporated in the genome of a host, a promoter of a gene (gene B) located downstream of the IRES is substituted by the promoter of the expression unit to change the temporal and spatial expression pattern of the gene B. In this case, it is possible to understand change in the expression pattern of the gene B by observing the expression of the reporter gene and observe the influence of this change in the expression pattern on phenotypic characters.

Further examples of the expression unit can include those comprising a promoter, gene A, IRES, gene B, and terminator arranged in this order, as shown in FIG. 2. In this case, transcription proceeds from the promoter toward downstream regions (direction indicated by the arrow in FIG. 2) up to the terminator in a host to produce mRNA. While the mRNA is translated through the translation mechanism of the host, both the gene A and the gene B are translated in this expression unit.

The gene A and the gene B are not particularly limited. Examples thereof can include a gene encoding the subunit of a protein assuming a dimeric structure. This can establish an expression system of the protein having a dimeric structure in a host without a polycistronic gene expression system. When either of the gene A or the gene B is used as a reporter gene, only a host having the expression of this reporter gene is selected. As a result, a transformed cell in which the other gene is expressed can be selected efficiently. Furthermore, it is also possible to produce trimeric or higher proteins in a host by inserting one or more (IRES+gene) units into between the gene B and the terminator.

The promoter contained in the expression unit is not particularly limited. For example, a promoter that tissue-specifically controls expression or a promoter that controls expression in response to some stimulus can be used to construct a tissue-specific or stimulus-responsive polycistronic gene expression system.

Particularly when the DNA (a) and/or (b) described in the paragraph "1-1. DNA according to the present invention" is used in the expression unit, it is preferred that several repeats of these DNAs should be linked to constitute the IRES. The number of the repeats is preferably 2 to 15, more preferably 5 to 10, even more preferably 7 to 10.

When the several repeats of the DNA (a) and/or (b) described in the paragraph "1-1. DNA according to the present invention" are linked, it is preferred that adjacent DNAs (a) and/or (b) should be linked directly without inserting a spacer sequence therebetween. The expression unit that contains the IRES where adjacent DNAs (a) and/or (b) are directly linked exhibits more excellent control ability than that exhibited by the expression unit having a spacer sequence inserted into between adjacent DNAs (a) and/or (b).

When the DNA (a) and/or (b) described in the paragraphs "1-2 and -3. DNA according to the present invention" is used in the expression unit, these DNAs can constitute the IRES for themselves.

When the IRES and the gene located downstream thereof are defined as one unit, the expression unit may have several units. In this case, the respective genes contained in the units can be expressed.

In this context, the gene (e.g., the "gene A" and the "gene B" shown in FIG. 2) contained in the expression unit is not particularly limited. Examples thereof can include a GUS gene encoding β-glucuronidase, a Luc gene encoding luciferase, a GFP gene encoding a green fluorescent protein, a kanamycin resistance gene, a hygromycin resistance gene, a hy5 gene encoding a photomorphogenesis-controlling protein, and an IgG gene encoding an antibody.

3. Transgenic Plant

A transgenic plant can be created by constructing the expression unit described in the paragraph "2. Expression unit" or a recombinant vector containing the expression unit, then transforming this expression unit or recombinant vector into a plant cell, and growing the transformed plant cells into a plant according to a standard method.

When the expression unit or the recombinant vector is used, a gene located downstream of the IRES is translated in the transformed cell and the transgenic plant even if the reading frame of a gene shifts where the IRES and the gene located downstream thereof are inserted. Thus, gene expression in the transformed cell and the transgenic plant can be examined efficiently by using the expression unit according to the present invention.

The recombinant vector can be obtained by ligating (inserting) the expression unit into an appropriate vector. Alternatively, the recombinant vector can be obtained by constructing the expression unit at a preferable position of an appropriate vector. An available vector is not particularly limited as long as it is capable of replication in a host. Examples thereof include plasmid DNA and phage DNA.

Examples of the plasmid DNA include *E. coli*-derived plasmids (e.g., pBR322, pBR325, pUC118, pUC119, pUC18, pUC19, and pBluescript), *Bacillus subtilis*-derived plasmids (e.g., pUB110 and pTP5), and yeast-derived plasmids (e.g., YEp13 and YCp50). Examples of the phage DNA include λ phages (e.g., Charon 4A, Charon 21A, EMBL3, EMBL4, λgt10, λgt11, and λZAP). Furthermore, animal viruses such as retroviruses or vaccinia viruses and insect virus vectors such as baculoviruses can also be used.

To insert the expression unit into a vector, a method is adopted, in which purified DNA having the expression unit is cleaved with an appropriate restriction enzyme and inserted into the restriction enzyme site or multicloning site of an appropriate vector. In addition to the expression unit, cis elements such as promoters and enhancers, splicing signal, poly-A addition signal, and selective markers, and so on can be ligated into the recombinant vector, if desired. Examples of the selective markers include dihydrofolate reductase genes, ampicillin resistance genes, and neomycin resistance genes.

The transformant can be obtained by introducing the recombinant vector into a host so that the gene contained in the expression unit is capable of expression. The plant to be transformed means any of the whole plant body, plant organs (e.g., leaves, petals, stems, roots, and seeds), plant tissues (e.g., epidermis, phloem, parenchyma, xylem, and vascular bundle), and cultured plant cells. Examples of the plant used in transformation include, but not limited to, plants belonging to the families Brassicaceae, Poaceae, Solanaceae, and Leguminosae (see the list below).

Solanaceae: tobacco (*Nicotiana tabacum*), potato (*Solamum tuberosum*)

Poaceae: maize (*Zea mays*), rice (*Oryza sativa*)

Malvaceae: cotton (*Gossypium hirsutum*), okra (*Abelmoschus esculentus*)

Brassicaceae: thale-cress (*Arabidopsis thaliana*), oilseed rape (*Brassica napus*)

Asteraceae: sunflower (*Helianthus annuus*), chrysanthemum (*Chrysanthemum indicum*)

Pedaliaceae: sesame (*Sesamum indicum*), castor-oil plant (*Ricimus communis*)

Oleaceae: olive (*Olea europaea*)

Myrtaceae: eucalyptus (*Eucalyptus globulus*), guava (*Psidium guajava*)

Rosaceae: rose (*Rosa sinnis*)

Theaceae: camellia (*Camellia japonica*)

Leguminosae: Chinese milk vetch (*Astragalus sinicus*), soybean (*Glycine max*)

Arecaceae: coconut (*Cocos mucifera*)

Sterculiaceae: cocoa (*Theobroma cacao*)

Rubiaceae: coffee tree (*Coffea arabica*)

The recombinant vector can be introduced into a plant by a typical transformation technique, for example, electroporation, an *Agrobacterium* method, a particular gun method, and a PEG method. For example, when the electroporation is used, the recombinant vector is introduced into a host by treatment under conditions of a voltage of 500 to 600 V, 1000 µF, and 20 msec with an electroporation apparatus equipped with a pulse controller. When the *Agrobacterium* method is used, the transformed plant can be obtained by introducing a constructed expression vector for plants into an appropriate *Agrobacterium* strain, for example *Agrobacterium tumefaciens*, and infecting the aseptically cultured leaf disc of a host with this strain according to, for example the vacuum infiltration method (Bechtold et al. (1993) C. R. Acad. Sci. Ser. III Sci. Vie, 316, 1194-1199). Alternatively, when the particle gun method is used, a plant body, organ, or tissue itself may be used directly or after being prepared into a section or into a protoplast. The sample thus prepared can be treated with a gene delivery apparatus (e.g., BIOLISTIC POS 1000/He; BioRad). Treatment conditions differ depending on plants or samples and usually are conditions of a pressure on the order of 1000 to 1100 psi and a distance on the order of 5 to 10 cm.

Tumor tissues, shoots, hairy roots, and so on, obtained as a result of transformation may be used directly in cell culture, tissue culture, or organ culture or can be regenerated into plants by use of a conventionally known plant tissue culture method by administering an appropriate concentration of plant hormone (e.g., auxin, cytokinin, gibberellin, abscisic acid, ethylene, and brassinolide) thereto.

EXAMPLES

Hereinafter, the present invention will be described more fully with reference to Examples. However, the technical scope of the present invention is not intended to be limited to these Examples.

Example 1

Figure 3:
FIG. 3 is a diagram showing the constitution of an expression vector used in Example 1.

At first, an expression vector having an expression unit was constructed as described below. The expression unit used in this Example is schematically shown in FIG. 3. In FIG. 3, "P35S" denotes a CaMV 35S promoter; "RLUC" denotes a gene encoding luciferase derived from sea pansy; "LUC" denotes a gene encoding luciferase derived from firefly; and "T3A" denotes a terminator sequence.

In this Example, 10 repeats of the nucleotide sequence of SEQ ID NO: 1 via spacer sequences, 10 repeats of the nucleotide sequence of SEQ ID NO: 1 without spacer sequences, the nucleotide sequence of SEQ ID NO: 2, and the nucleotide sequence of SEQ ID NO: 4 were prepared as IRES. The spacer sequences were "CAT" located upstream of the nucleotide sequence of SEQ ID NO: 1 and "TTCTGA" located downstream thereof.

A vector used in gene expression in a plant was created from pPZP200 used as a source. The pPZP200 is a vector reported by Hajdukiewicz, P. et al. (Hajdukiewicz, P., Svab, Z. and Maliga, P. (1994) the small, versatile pPZP family of *Agrobacterium* binary vectors for plant transformation. Plant Mol Biol 25, 989-994), which allows for the recombination of genes to the chromosome of a plant via *Agrobacterium* strains. "P35S" and "RLUC" were inserted into a HindIII site in the multicloning site of the pPZP200. Next, a kanamycin resistance gene and a nopaline synthase gene promoter and terminator were inserted into KpnI and EcoRI sites thereof Then, "LUC" and "T3A" were inserted into BanHI and KpnI sites thereof Finally, the sequence having activity as IRES was inserted into SalI and BamHI sites thereof The "P35S" used here is a sequence that can be amplified by PCR using pBI221 reported by Jefferson, R. A. et al. (Jefferson, R. A., Kavanagh, T. A. and Bevan, M. W. (1987) GUS fusions: β-glucuronidase as a sensitive and versatile gene fusion marker in higher plants. EMBO J. 6, 3901-3907) as a template. The "RLUC" is a sequence that can be amplified by PCR using pRL-TK sold by Promega as a template. The kanamycin resistance gene and the nopaline synthase gene promoter and terminator are sequences that can be amplified by PCR using Bin19 reported by David A. Frisch et al. (David A. F., Larry W. H., Nathaniel, T. Y., Terry, L. T., Susan, H. H. and Timothy, C. H. (1995) Complete Sequence of the binary vector Bin19. Plant Mol Biol 27, 405-409) as a template. The "LUC" and the "T3A" are sequences that can be amplified by PCR using yy211 reported by Kimura, M. et al. (Kimura, M., Yoshizumi, T., Manabe, T., Yamamoto, Y. Y. and Matsui, M. (2001) Arabidopsis transcriptional regulation by light stress via hydrogen peroxide-dependent and -independent pathways. Genes Cells, 6, 607-617) as a template. The sequence used as IRES can be obtained from those chemically synthesized by, for example SIGMA Genosys.

For comparison, a vector where a gene encoding firefly-derived luciferase and a terminator sequence were ligated in this order downstream of a CaMV 35S promoter and a vector where a gene encoding sea pansy-derived luciferase, a gene encoding firefly-derived luciferase, and a terminator sequence were ligated in this order downstream of a CaMV 35S promoter were prepared as expression vectors without IRES. Moreover, for comparison, a vector where a gene encoding sea pansy-derived luciferase, ECMV, a gene encoding firefly-derived luciferase, and a terminator sequence were ligated in this order downstream of a CaMV 35S promoter was prepared as an expression vector having ECMV (see Plant J. 24, 583-589) known to function as IRES in mammal cells and tobacco.

Example 2

The expression vector prepared in Example 1 was used to create transgenic plants as described below.

At first, the expression vector created from the pPZP200 used as a source was used to create transformants with reference to the Dipping method mediated by *Agrobacterium* infection. The Dipping method is a transformation technique introduced by Clough S. J. et al. (Clough, S. J. and Bent, A. F. (1998) floral dip: a simplified method for *Agrobacterium*-mediated transformation of *Arabidopsis thaliana*. Plant J. 16(6)735-743).

In this context, *Agrobacterium* strains (C58C1Rif line) used in infection were transformed with the pPZP200 vector. The C58C1Rif line is a line reported to be used by Osumi (Teruko Osumi (2001) *Agrobacterium* direct injection method "New Edition, Experimental Protocol of Model Plant 105-108"). By the day, the strains were grown in 200 ml of LB culture medium until $OD_{600}$ reached approximately 1.2 to 1.5. The strains were collected at room temperature and suspended in 300 ml of Dipping solution described below.

*Arabidopsis* (Col line) used in infection was grown so that the day of infection fell on approximately 1 week after bolting. The Col line is available form Sendai *Arabidopsis* Seed Stock Center.

The grown *Arabidopsis* plants were immersed in an inverted position in the Dipping solution so that the whole flower stalks were contacted therewith. After immersion for approximately 30 seconds, the plants were put back into position. After infection, the plants were kept covered with a bag for several days with ambient humidity kept high. Then, the plants were grown in a normal environment.

After approximately 1 month, seeds were harvested. The harvested seeds were allowed to germinate on an agar medium containing 75 µg/ml kanamycin to select only resistance individuals. Transgenic plants having the foreign genes shown in FIG. 3 were selected by these procedures.

Dipping solution (composition)
0.044 µM benzylaminopurine
5% Sucrose
0.02% SILWET L-77 (an organosilicone surfactant)
1/2 X MS salt
1/2 X Gamborg B5 vitamin
0.5 g/l MES Example 3

The transgenic plants created in Example 2 were measured as described below for the fluorescence levels of sea pansy-derived luciferase and firefly-derived luciferase.

Specifically, at first, 1 or 2 true leaves of the transgenic plant were supplemented with 1 ml of Passive Lysis Buffer of Dual Luciferase Assay Kit (manufactured by Promega) cooled at 4° C., and gradually ground. The ground solution was centrifuged for 30 minutes under conditions of 4° C. and 17800 g. The obtained supernatant was used for the measurement.

Specifically, a 20-µl aliquot of the supernatant was mixed with 100 µl of Luciferase Assay Reagent II of Dual Luciferase Assay Kit (manufactured by Promega). After mixing by pipetting, light developed from the reaction between a substrate luciferin contained in the Reagent and the firefly-derived luciferase protein in the sample was quickly measured with a scintillation counter. After measurement, the mixture sample was further supplemented with 100 µl of Stop & Glo of Dual Luciferase Assay Kit (manufactured by Promega). After mixing by vortex, light developed from the reaction between a substrate coelenterazine contained in the Reagent and the sea pansy-derived luciferase protein in the sample was quickly measured with a scintillation counter.

Figure 4:
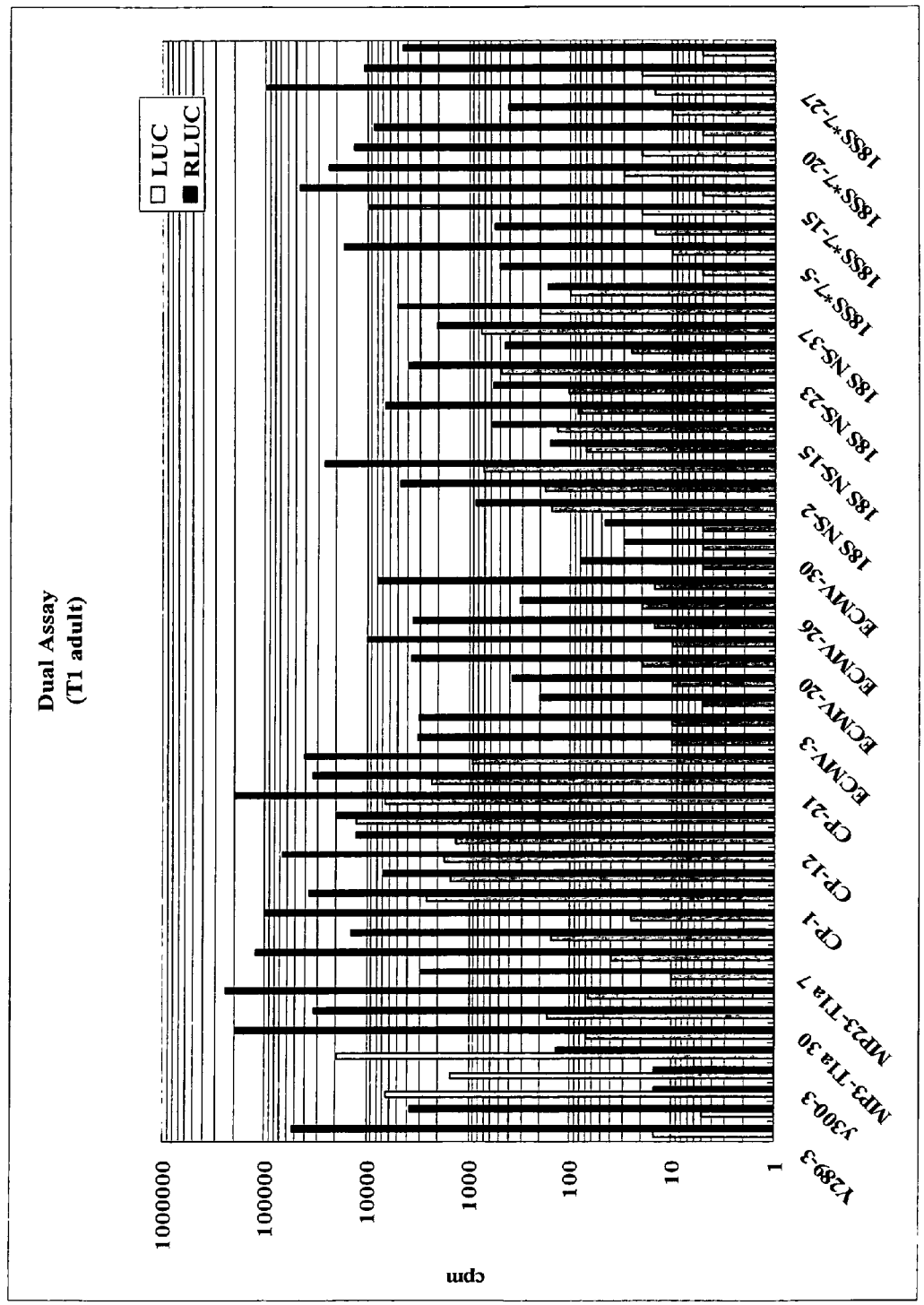
FIG. 4 is a diagram showing a result of measuring a transgenic plant created in Example 2 for the luminescence levels of sea pansy-derived luciferase and firefly-derived luciferase.

The result of measuring the transgenic plant created in Example 2 for the fluorescence levels of sea pansy-derived luciferase and firefly-derived luciferase is shown in FIG. 4. In FIG. 4, "18S NS-2", "18S NS-15", "18S NS-23", and "18S NS-37" denote transgenic plants created by using the expression vector where 10 repeats of the nucleotide sequence of SEQ ID NO: 1 without spacer sequences served as IRES; "18SS*7-5", "18SS*7-15", "18SS*7-20", and "18SS*7-27" denote transgenic plants created by using the expression vector where 10 repeats of the nucleotide sequence of SEQ ID NO: 1 via spacer sequences served as IRES; "MP3-T1a 30" and "MP3-T1a 7" denote transgenic plants created by using the expression vector where the nucleotide sequence of SEQ ID NO: 2 served as IRES; and "CP-1", "CP-12", and "CP-21" denote transgenic plants created by using the expression vector where the nucleotide sequence of SEQ ID NO: 2 served as IRES.

In FIG. 4, "Y289-3" denotes a comparative example and a transgenic plant created by using the expression vector where a gene encoding sea pansy-derived luciferase, a gene encoding firefly-derived luciferase, and a terminator sequence were ligated in this order downstream of a CaMV 35S promoter; "y300-3" denotes a comparative example and a transgenic plant created by using the expression vector where a gene encoding firefly-derived luciferase and a terminator sequence were ligated in this order downstream of a CaMV 35S promoter; and "ECMV-3", "ECMV-20", "ECMV-26", and "ECMV-30" denote transgenic plants created by using the expression vector where a gene encoding sea pansy-derived luciferase, ECMV, a gene encoding firefly-derived luciferase, and a terminator sequence were ligated in this order downstream of a CaMV 35S promoter.

As shown in FIG. 4, when the DNA having 10 repeats of the nucleotide sequence of SEQ ID NO: 1 without spacer sequences was used as IRES, the luminescence level of the firefly-derived luciferase located downstream of the IRES was far increased. It was thus demonstrated that this IRES can positively control the translation efficiency of the firefly-derived luciferase. Similarly, when the DNA consisting of the nucleotide sequence of SEQ ID NO: 3 was used as IRES, the fluorescence level of the firefly-derived luciferase located downstream of the IRES was far increased. It was thus demonstrated that this IRES can positively control the translation efficiency of the firefly-derived luciferase.

On the other hand, when the DNA having 10 repeats of the nucleotide sequence of SEQ ID NO: 1 via spacer sequences and the DNA consisting of the nucleotide sequence of SEQ ID NO: 2 were used as IRES, the fluorescence level of the firefly-derived luciferase located downstream of the IRES was slightly increased. It was thus demonstrated that this IRES can slightly positively control the translation efficiency of the firefly-derived luciferase.

By contrast, when the ECMV was used as IRES, the fluorescence level of the firefly-derived luciferase located downstream of the IRES could not be increased.

All publications, patents, and patent applications cited herein are incorporated herein by reference in their entirety.

The invention claimed is:

1. An isolated polynucleotide which functions as an IRES (internal ribosome entry site) in a plant and comprises two to fifteen repeats of the nucleotide sequence represented by SEQ ID NO: 1 without a spacer sequence.

2. The polynucleotide according to claim 1, wherein the polynucleotide further comprises at least a coding region and/or a promoter.

3. A vector comprising the polynucleotide according to claim 1.

4. A transformant transformed with the polynucleotide according to claim 1.

5. A transgenic plant having the polynucleotide according to claim 1 incorporated in the genome.

6. A method of regulating gene expression in a plant, said method comprising:
 constructing the polynucleotide according to claim 1; and
 transforming the polynucleotide into a plant host,
 wherein the translation of a gene located downstream of the repeats of the nucleotide sequence represented by SEQ ID NO: 1 is positively regulated in the transformed host.

7. A transformant transformed with the vector according to claim 3.

8. A method of regulating gene expression in a plant, said method comprising:

constructing the vector according to claim 3; and
transforming the vector into a plant host,
wherein the translation of a gene located downstream of the repeats of the nucleotide sequence represented by SEQ ID NO: 1 is positively regulated in the transformed host.

* * * * *

SEQUENCE LISTING

<160> NUMBER OF SEQ ID NOS: 37

<210> SEQ ID NO 1
<211> LENGTH: 12
<212> TYPE: DNA

<213> ORGANISM: Artificial Sequence
<220> FEATURE:
<223> OTHER INFORMATION: Description of Artificial Sequence: Synthetic
      DNA sequence

<400> SEQUENCE: 1
gccagcggag tc                                                              12

<210> SEQ ID NO 2
<211> LENGTH: 136
<212> TYPE: DNA
<213> ORGANISM: Tobamovirus Ob

<400> SEQUENCE: 2
gtattttcca cagttagatg aggccgttgc cgaggttcat aagaccgcgg taggcggttc        60
gtttgctttt tgtagtataa ttaaatattt gtcagataag agattgttta gagatttgtt       120
ctttgtttga taatgt                                                        136

<210> SEQ ID NO 3
<211> LENGTH: 80
<212> TYPE: DNA
<213> ORGANISM: Tobamovirus Ob

<400> SEQUENCE: 3
gttcgtttgc tttttgtagt ataattaaat atttgtcaga taagagattg tttagagatt        60
tgttctttgt tgataatgt                                                      80

<210> SEQ ID NO 4
<211> LENGTH: 148
<212> TYPE: DNA
<213> ORGANISM: Tobamovirus Ob

<400> SEQUENCE: 4
gaattcgtcg attcggttgc agcatttaaa gcggttgaca actttaaaag aaggaaaaag        60
aaggttgaag aaaagggtgt agtaagtaag tataagtaca gaccggagaa gtacgccggt       120
cctgattcgt ttaatttgaa agaagaaa                                          148

<210> SEQ ID NO 5
<211> LENGTH: 12
<212> TYPE: DNA
<213> ORGANISM: Glycine max

<400> SEQUENCE: 5
gccagcggag tc                                                              12

<210> SEQ ID NO 6
<211> LENGTH: 12
<212> TYPE: DNA
<213> ORGANISM: Petunia sp.

<400> SEQUENCE: 6
gccagcggag tc                                                              12

<210> SEQ ID NO 7
<211> LENGTH: 12
<212> TYPE: DNA
<213> ORGANISM: Lycopersicon esculentum

<400> SEQUENCE: 7
gccggcggag tc                                                              12

<210> SEQ ID NO 8
<211> LENGTH: 12
<212> TYPE: DNA
<213> ORGANISM: Antirrhinum sp.

<400> SEQUENCE: 8
gccggcggag tc                                                                12

<210> SEQ ID NO 9
<211> LENGTH: 12
<212> TYPE: DNA
<213> ORGANISM: Nicotiana tabacum

<400> SEQUENCE: 9
gccggcggag tc                                                                12

<210> SEQ ID NO 10
<211> LENGTH: 12
<212> TYPE: DNA
<213> ORGANISM: Oryza sativa

<400> SEQUENCE: 10
gccggcggag tc                                                                12

<210> SEQ ID NO 11
<211> LENGTH: 12
<212> TYPE: DNA
<213> ORGANISM: Zea mays

<400> SEQUENCE: 11
gccagcgggg tc                                                                12

<210> SEQ ID NO 12
<211> LENGTH: 12
<212> TYPE: DNA
<213> ORGANISM: Medicago polymorpha

<400> SEQUENCE: 12
gccggcggag tc                                                                12

<210> SEQ ID NO 13
<211> LENGTH: 12
<212> TYPE: DNA
<213> ORGANISM: Physcomitrella patens

<400> SEQUENCE: 13
gctggcggag tc                                                                12

<210> SEQ ID NO 14
<211> LENGTH: 12
<212> TYPE: DNA
<213> ORGANISM: Chlamydomonas sp.

<400> SEQUENCE: 14
gctggcaggg tc                                                                12

<210> SEQ ID NO 15
<211> LENGTH: 12
<212> TYPE: DNA
<213> ORGANISM: Synechocystis sp.

<400> SEQUENCE: 15
acggctcggg tc                                                                12

-continued

<210> SEQ ID NO 16
<211> LENGTH: 12
<212> TYPE: DNA
<213> ORGANISM: Saccharomyces cerevisiae

<400> SEQUENCE: 16
accgagtggg tc                                              12

<210> SEQ ID NO 17
<211> LENGTH: 12
<212> TYPE: DNA
<213> ORGANISM: Schizosaccharomyces pombe

<400> SEQUENCE: 17
gccgagcaag tc                                              12

<210> SEQ ID NO 18
<211> LENGTH: 12
<212> TYPE: DNA
<213> ORGANISM: Mus musculus

<400> SEQUENCE: 18
gcccggcggg tc                                              12

<210> SEQ ID NO 19
<211> LENGTH: 12
<212> TYPE: DNA
<213> ORGANISM: Rattus norvegicus

<400> SEQUENCE: 19
gcccggcggg tc                                              12

<210> SEQ ID NO 20
<211> LENGTH: 12
<212> TYPE: DNA
<213> ORGANISM: Homo sapiens

<400> SEQUENCE: 20
gcccggcggg tc                                              12

<210> SEQ ID NO 21
<211> LENGTH: 57
<212> TYPE: DNA
<213> ORGANISM: Arabidopsis sp.

<400> SEQUENCE: 21
gatcagcgga tgttgcttat aggactccgc tggcacctta tgagaaatca aagtttt          57

<210> SEQ ID NO 22
<211> LENGTH: 57
<212> TYPE: DNA
<213> ORGANISM: Glycine max

<400> SEQUENCE: 22
gatcagcgga tgttgctttt aggactccgc tggcacctta tgagaaatca aagtctt          57

<210> SEQ ID NO 23
<211> LENGTH: 57
<212> TYPE: DNA
<213> ORGANISM: Petunia sp.

<400> SEQUENCE: 23
gatcagcgga tgttgctttt aggactccgc tggcaccttt tgagaaatca aagtttt    57

<210> SEQ ID NO 24
<211> LENGTH: 57
<212> TYPE: DNA
<213> ORGANISM: Lycopersicon sp.

<400> SEQUENCE: 24
gatcggcgga tgttgctttt aggactccgc cggcaccttt tgagaaatca aagtttt    57

<210> SEQ ID NO 25
<211> LENGTH: 57
<212> TYPE: DNA
<213> ORGANISM: Antirrhinum sp.

<400> SEQUENCE: 25
gatcggcgga tgttgctttt aggactccgc cggcaccttt tgagaaatca aagtctt    57

<210> SEQ ID NO 26
<211> LENGTH: 57
<212> TYPE: DNA
<213> ORGANISM: Nicotiana tabacum

<400> SEQUENCE: 26
gatcggcgga tgttgctttt aggactccgc cggcaccttt tgagaaatca aagtttt    57

<210> SEQ ID NO 27
<211> LENGTH: 57
<212> TYPE: DNA
<213> ORGANISM: Oryza sativa

<400> SEQUENCE: 27
gatcggcgga tgttgcttat aggactccgc cggcaccttt tgagaaatca aagtctt    57

<210> SEQ ID NO 28
<211> LENGTH: 57
<212> TYPE: DNA
<213> ORGANISM: Zea mays

<400> SEQUENCE: 28
gatcagcggt gttactaata ggaccccgct ggccaccttt tgagaaatca aagtctt    57

<210> SEQ ID NO 29
<211> LENGTH: 58
<212> TYPE: DNA
<213> ORGANISM: Medicago polymorpha

<400> SEQUENCE: 29
gatcggcgga tgttaatttg atgactccgc cggcacctcc atgagaaatc aaagtttt    58

<210> SEQ ID NO 30
<211> LENGTH: 57
<212> TYPE: DNA
<213> ORGANISM: Physcomitrella patens

<400> SEQUENCE: 30
gattggcgga tgttactttg atgactccgc cagcaccttt tgagaaatca aagtttt    57

<210> SEQ ID NO 31
<211> LENGTH: 57
<212> TYPE: DNA
<213> ORGANISM: Chlamydomonas sp.

<400> SEQUENCE: 31

```
<210> SEQ ID NO 32
<211> LENGTH: 43
<212> TYPE: DNA
<213> ORGANISM: Synechocystis sp.

<400> SEQUENCE: 32
gcgtggcttg tatcgacccg agccgtgccg aagctaacgc gtt                    43

<210> SEQ ID NO 33
<211> LENGTH: 56
<212> TYPE: DNA
<213> ORGANISM: Saccharomyces cerevisiae

<400> SEQUENCE: 33
atcgggtggt gtttttttaa tgacccactc ggtaccttac gagaaatcaa agtctt     56

<210> SEQ ID NO 34
<211> LENGTH: 58
<212> TYPE: DNA
<213> ORGANISM: Schizosaccharomyces pombe

<400> SEQUENCE: 34
gatcgggcaa tgtttcattt atcgacttgc tcggcacctt acgagaaatc aaagtctt   58

<210> SEQ ID NO 35
<211> LENGTH: 57
<212> TYPE: DNA
<213> ORGANISM: Mus musculus

<400> SEQUENCE: 35
gatgcggcgg cgttattccc atgacccgcc gggcagcttc cgggaaacca aagtctt    57

<210> SEQ ID NO 36
<211> LENGTH: 57
<212> TYPE: DNA
<213> ORGANISM: Rattus norvegicus

<400> SEQUENCE: 36
gatgcggcgg cgttattccc atgacccgcc gggcagcttc cgggaaacca aagtctt    57

<210> SEQ ID NO 37
<211> LENGTH: 57
<212> TYPE: DNA
<213> ORGANISM: Homo sapiens

<400> SEQUENCE: 37
gatgcggcgg cgttattccc atgacccgcc gggcagcttc cgggaaacca aagtctt    57
```